United States Patent [19]

Syed et al.

[11] Patent Number: 5,348,737
[45] Date of Patent: Sep. 20, 1994

[54] COMPOSITION AND PROCESS FOR DECREASING HAIR FIBER SWELLING

[75] Inventors: Ali N. Syed, Orland Park; Kaleem Ahmad, Chicago, both of Ill.

[73] Assignee: Avlon Industries, Inc., Chicago, Ill.

[21] Appl. No.: 95,614

[22] Filed: Jul. 21, 1993

[51] Int. Cl.$^5$ .............................. A61K 7/09; A61K 7/11
[52] U.S. Cl. ...................................... 424/71; 132/203; 132/204
[58] Field of Search .................... 424/71; 132/203, 204

[56] References Cited

U.S. PATENT DOCUMENTS

| | | | |
|---|---|---|---|
| 2,817,342 | 12/1957 | Henkin | 106/125 |
| 3,472,243 | 10/1969 | Wall | 106/125 |
| 3,628,974 | 12/1971 | Battista | 106/125 |
| 3,633,591 | 1/1972 | Anzulno | 132/204 |
| 3,842,847 | 10/1974 | Hewitt et al. | 132/202 |
| 3,957,065 | 5/1976 | Busch et al. | 132/204 |
| 4,314,573 | 2/1982 | Spitzer et al. | 132/202 |
| 4,416,297 | 11/1983 | Wolfram et al. | 132/7 |
| 4,530,830 | 7/1985 | McKaba et al. | 424/71 |
| 4,581,229 | 4/1986 | Petrow | 424/70 |
| 4,660,580 | 4/1987 | Hoch et al. | 132/204 |
| 4,839,165 | 6/1989 | Hoppe et al. | 424/70 |
| 4,840,791 | 6/1989 | Mathews et al. | 424/71 |
| 5,047,233 | 9/1991 | Mathews et al. | 424/72 |

OTHER PUBLICATIONS

A. Shansky, "The Osmotic Behavior Hair During the Permanent Waving Process as Explained by Swelling Measurements", 1963 *Journal of Society of Cosmetic Chemists*, 420.

J. Nothen, V. Bollert, G. Blankenburg, and H. Kocker, "The Influence of Osmotic Swelling Behavior on the Quality of the Permanent Wave", Proceedings of the 16th IFSCC Congress, vol. 1 at 315 (1990).

R. Y. Lochhead, J. Randy Wright, Lon J. Mathias, "A Direct Real-Time Visual Study of the Morphological Chances in Hair Which Accompany Cosmetic Treatment", Society of Cosmetic Chemists, May 2–3, 1991, pp. 9–12.

*Primary Examiner*—Thurman K. Page
*Assistant Examiner*—Jyothsna Vencat

[57] ABSTRACT

A process for relaxing hair in which the hair fibers undergo minimal swelling is provided, using a composition that decreases the swelling of hair fibers. Use of the composition or process decreases hair fiber swelling during the relaxing process, thereby decreasing structural damage to the hair while increasing hair fiber strength.

9 Claims, 2 Drawing Sheets

COMPOSITION AND PROCESS FOR DECREASING HAIR FIBER SWELLING

FIELD OF THE INVENTION

This invention relates generally to the chemical processing of hair fibers, and more particularly to a composition and process for decreasing hair fiber swelling during the process of lanthionizing hair fibers.

BACKGROUND OF THE INVENTION

Human hair has a variety of textures, from fine to coarse, and from straight to curly. In today's society, the ability to alter or change the texture of one's hair through chemical processes is important to both men and women. Hair care products and chemical processes that can alter the texture of hair are in great demand. Among individuals with excessively curly hair, products and processes that straighten or "relax" hair are especially popular, for such products and processes increase hair manageability and ease of styling.

The relaxing process operates by changing the chemical structure of the hair fibers. Hair fibers are comprised of keratin, which is in turn comprised of polypeptide chains bonded together by three types of bonds: cystine (or disulfide) bonds hydrogen bonds, and salt linkages. The relaxing process operates primarily on the cystine bonds. When the cystine bonds are exposed to an alkaline relaxing solution, they are transformed to lanthionine bonds. The chemical term for the hair relaxing process is lanthionization.

In the conventional relaxing process, an alkaline relaxing solution is first applied to the hair for eighteen to, twenty minutes. During this step, hair gradually becomes physically straighter. After the alkaline relaxing solution has been left on the hair for eighteen to twenty minutes, it is rinsed from the hair with water for one to three minutes. Directions for use of conventional relaxing systems stress the importance of ensuring that the alkaline relaxing solution is left on the hair for no longer than twenty minutes. It is taught that if the relaxing solution is left on the hair for longer than twenty minutes, the hair will be overprocessed, and excessively damaged Although the conventional relaxing process decreases the amount of curl in hair, it also damages hair. The conventional process causes hair fibers longitudinally to split and break, leaving hair coarse, brittle, and unmanageable. These negative results cannot be corrected by applying conditioning agents to the hair subsequent to the relaxing process. Therefore, individuals wishing to straighten their hair using the conventional relaxing process must suffer the damaging structural effects of the process on their hair.

It is also known that hair fibers swell in the presence of water, and that excessive swelling can also result in structural damage to the fibers. Swelling occurs in both the hair fiber cortex and the hair fiber cuticle-the respective inner and outer portions of the hair fiber. Structural damage to the fiber occurs when the cortex continues to swell after the cuticle has ceased swelling, causing the cuticle and cortex to rupture, thereby rendering the hair damaged, dull, and difficult to manage. Although this swelling phenomenon has been identified, the question of how to avoid the swelling and resulting structural damage to hair during the relaxing process has remained commercially unanswered.

Thus, the conventional relaxing process suffers from the disadvantage of causing excessive swelling of hair fibers and resulting in structural damage to the fibers.

Accordingly, it is an object of the present invention to provide a composition for use during the hair relaxing process to decrease swelling of hair fibers during the hair relaxing process, thereby decreasing structural damage to the fibers.

Another object of the invention is to provide a composition to decrease swelling of hair fibers during the hair relaxing process while also strengthening the hair.

Yet another object of the invention is to provide a process for relaxing hair fibers during which hair fibers undergo minimal swelling.

A still further object of the invention is to provide a process for relaxing hair fibers that includes the use of a composition to decrease the swelling of the hair fibers and strengthen the hair fibers during the process.

Other objects and advantages of the invention will become apparent upon reading the following detailed description.

SUMMARY OF THE INVENTION

A process for relaxing hair in which the hair fibers undergo minimal swelling is provided. The process employs a deswelling composition. In the process, hair fibers are lanthionized with a non-reducing base. The deswelling composition is then applied to the hair fibers, prior to removal of the nonreducing base. Use of the composition or process decreases hair fiber swelling during lanthionization, thereby decreasing structural damage to the hair while increasing hair fiber strength.

DETAILED DESCRIPTION OF A PREFERRED EMBODIMENT

Figure 1:
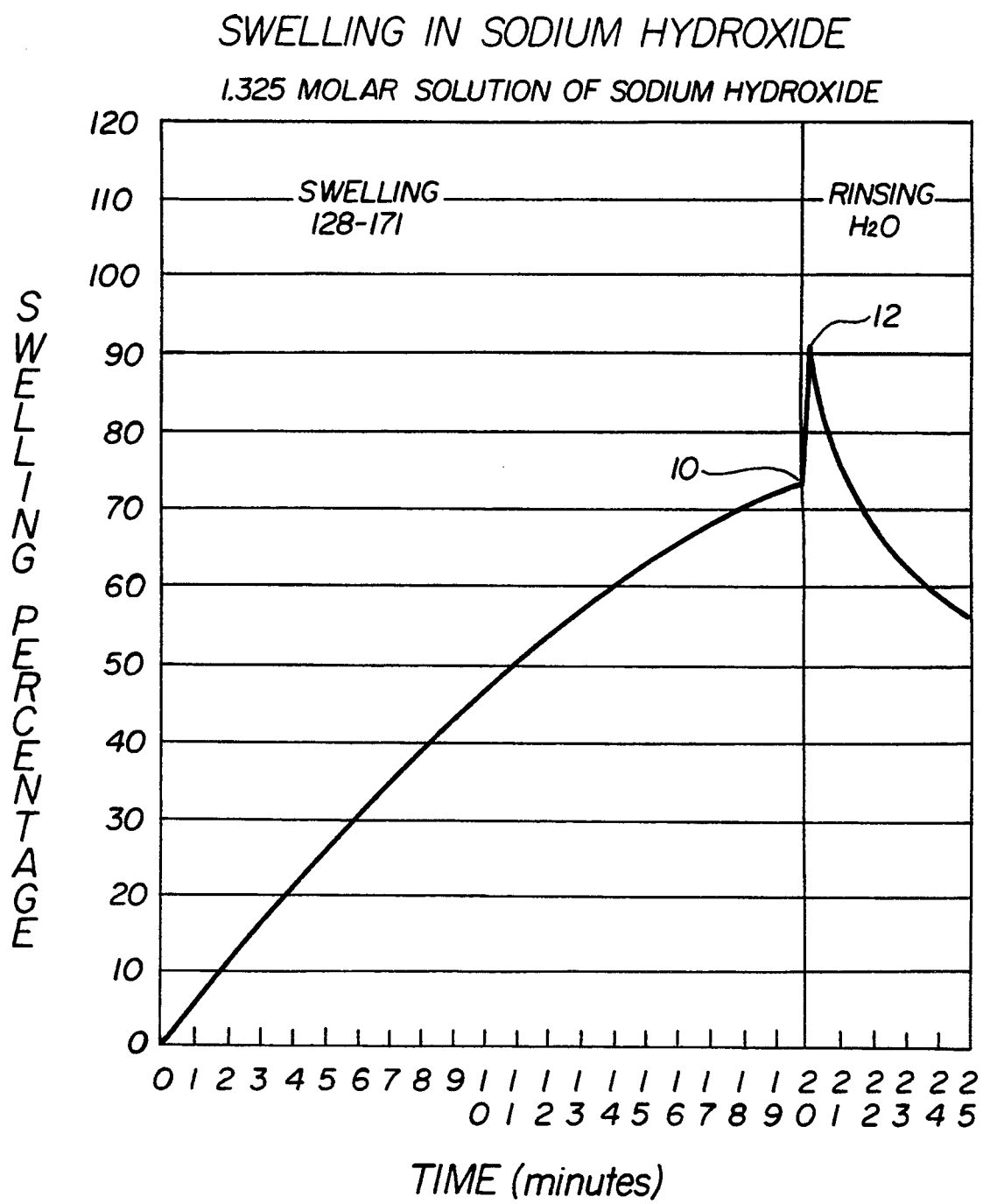
FIG. 1 is a graph illustrating the results of an analysis of the swelling of hair fibers relaxed according to the conventional relaxing process.

The present invention is a novel hair relaxing process employing a deswelling composition. The deswelling composition of the present invention comprises a starch, sugar, or salt, and a pH-decreasing agent.

The process of the present invention includes a first step in which the hair fibers are lanthionized, and a second step in which the hair fibers are deswelled. In the first step, the hair is lanthionized by a hair-relaxing solution. Hair fibers are lanthionized by applying the relaxing solution for ten to twenty minutes so the curl of the hair physically relaxes. Any commercially-available hair relaxing solution may be used for this step. Such solutions typically contain, as the active ingredient, approximately 2.4 percent of a non-reducing base such as sodium hydroxide, and typically have a pH between 12.0 to 13.5. One suitable product is AFFIRM® Creme Relaxer, available from Avlon Industries, Inc., P.O. Box 388080, Chicago, Ill. 60638.

Thereafter, a deswelling composition is applied directly to the hair for about two to five minutes, before rinsing the relaxing solution. In this respect, the process of the present invention differs radically from the conventional relaxing process. In the conventional processes, the relaxing solution is rinsed from the hair with water after eighteen to twenty minutes. It is taught in such processes that if the relaxing solution is left on the hair longer than twenty minutes, the hair will undergo greater structural damage.

In the process of the present invention, however, the relaxing solution can remain on the hair longer than twenty minutes. After the relaxing solution has been on the hair for about twenty minutes, the deswelling composition is applied directly on the hair, without rinsing the relaxing solution. The deswelling composition remains on the hair for approximately two to five minutes. After the composition of the present invention is applied to the hair for this period, the hair is rinsed with water for approximately one to two minutes.

In an alternate embodiment of the invention, the composition of the present invention is reapplied to the hair for approximately three to five minutes after the rinse. Used this way, the composition of the present invention also conditions the hair. The hair is then rinsed with water for approximately one to two minutes, and styled. Another alternate embodiment of the invention includes using the deswelling composition in combination with the water rinse. This embodiment would involve the use of a deswelling solution diluted with water for use as a deswelling rinse.

One preferred embodiment of the deswelling composition of the present invention comprises an aqueous solution or dispersion containing a hydrogenated starch hydrolysate and a pH-decreasing agent. Other embodiments of the deswelling composition comprise a salt, a starch, or a sugar, and a pH-decreasing agent. Specific examples of suitable salts, starches, and sugars include sodium lactate, glycerol, sorbitol, sucrose, glucose, fructose, magnesium sulfate, sodium acetate, and combinations thereof. The pH decreasing agent is preferably a non-caustic acid. Specific examples of suitable pH-decreasing agents include lactic acid, phosphoric acid, any organic acid, any mineral acid, and combinations thereof. Ingredients inert to the action of the deswelling composition (such as conditioners) can also be included in the deswelling composition. The hydrogenated starches used include those sold under the commercial names Hystar 7000, Hystar 6075, Hystar HM-75 and Hystar CG, all available from Lonza, Inc., 17–17 Route 208, Fair Lawn, N.J.

Preferable ranges for the components of an embodiment of the deswelling composition of the present invention are set forth in Table 1.

TABLE 1

| MATERIAL | QUANTITIES INTRODUCED (approximate range of parts by weight) |
| --- | --- |
| Hydrogenated Starch Hydrolysate (70%) | 10.00–95.00 |
| Lactic Acid (85%) | 0.00–12.00 |
| Phosphoric Acid (85%) | 0.00–12.00 |
| Cationic Polymer | 0.25–5.00 |
| Ethoxylated (7 mole) Fatty Acid | 0.10–5.00 |
| Hydrolysed Protein | 0.25–5.00 |

Water comprises the remaining portion of the composition from about 87 percent to about 0 percent by weight. A suitable cationic polymer is that sold under the trade name MERQUAT 100 by Calgon Corp., P.O. Box 1346, Pittsburgh, Penna. 15230, Suitable hydrolysed proteins are sold under the trade names Hydrolyzed Wheat Protein and Wheat Oligosaccharides, available from Croda, Inc., 183 Madison Avenue, New York, N.Y. 10016.

The following embodiments further exemplify the deswelling composition of the present invention.

EXAMPLE 1

| MATERIAL | QUANTITIES INTRODUCED (parts by weight) |
| --- | --- |
| Deionized water | 28.20 |
| Hystar CG (70%) | 56.60 |
| Lactic Acid (85%) | 6.40 |
| Cationic Polymer | 2.00 |
| Hydrolyzed Protein | 0.50 |
| Ethoxylated (7 mole) Fatty Acid | 0.30 |
| Phosphoric Acid (85%) | 6.40 |

To prepare the composition, deionized water, Hystar CG, lactic acid, cationic polymer, and hydrolyzed protein were mixed with a T-Line Laboratory Stirrer manufactured by Talboys Engineering Corp., Montrose, Penna. The mixture was heated to 45° C. Ethoxylated fatty acid was then added to the mixture. The mixture was mixed for ten to fifteen minutes, until homogenous. The mixture was then cooled to room temperature. The pH was then adjusted with phosphoric acid to 0.5. Phosphoric acid is the primary pH-reducing agent. Although lactic acid is primarily used for its moisturizing properties, it also acts as a pH-decreasing agent.

EXAMPLE 2

| MATERIAL | QUANTITIES INTRODUCED (parts by weight) |
| --- | --- |
| Deionized water | 28.20 |
| Hystar 7000 (70%) | 56.60 |
| Lactic Acid (85%) | 6.00 |
| Cationic Polymer | 2.00 |
| Hydrolyzed Protein | 0.50 |
| Ethoxylated (7 mole) Fatty Acid | 0.30 |
| Phosphoric Acid (85%) | 6.40 |

The composition was prepared as set forth in Example 1.

EXAMPLE 3

| MATERIAL | QUANTITIES INTRODUCED (parts by weight) |
| --- | --- |
| Deionized water | 28.20 |
| Hystar 6075 (70%) | 56.60 |
| Lactic Acid (85%) | 6.00 |
| Cationic Polymer | 2.00 |
| Hydrolyzed Protein | 0.50 |
| Ethoxylated (7 mole) Fatty Acid | 0.30 |
| Phosphoric Acid (85%) | 6.40 |

The composition was prepared as set forth in Example 1.

EXAMPLE 4

| MATERIAL | QUANTITIES INTRODUCED (parts by weight) |
| --- | --- |
| Deionized water | 28.20 |
| Hystar HM-75 (70%) | 56.60 |
| Lactic Acid (85%) | 6.00 |
| Cationic Polymer | 2.00 |
| Hydrolyzed Protein | 0.50 |
| Ethoxylated (7 mole) Fatty | 0.30 |

-continued

EXAMPLE 4

| MATERIAL | QUANTITIES INTRODUCED (parts by weight) |
|---|---|
| Acid | |
| Phosphoric Acid (85%) | 6.40 |

The composition was prepared as set forth in Example 1.

EXAMPLE 5

| MATERIAL | QUANTITIES INTRODUCED (parts by weight) |
|---|---|
| Deionized water | 28.20 |
| Hystar CG (70%) | 56.60 |
| Magnesium Sulfate | 5.86 |
| Lactic Acid (85%) | 6.00 |
| Cationic Polymer | 2.00 |
| Hydrolyzed Protein | 0.50 |
| Ethoxylated (7 mole) Fatty Acid | 0.30 |
| Phosphoric Acid (85%) | 6.40 |

The composition was prepared as set forth in Example 1.

EXAMPLE 6

| MATERIAL | QUANTITIES INTRODUCED (parts by weight) |
|---|---|
| Deionized water | 71.65 |
| Magnesium Sulfate | 21.95 |
| Phosphoric Acid (85%) | 6.40 |

Deionized water and magnesium sulfate were weighed into a beaker and mixed with a Lightning propeller mixer. The mixture was heated to 50° C. The mixture was stirred until clear, and then cooled to 25° C. The pH was then adjusted to 0.5.

It is believed that the deswelling composition of the present invention decreases the swelling of the hair fiber by reducing the osmotic pressure in the fiber. During the first step of the relaxing process, the non-reducing base of the relaxing solution penetrates the hair fiber. Because the hair fiber acts as a semi-permeable membrane, osmotic pressure builds up within the fiber, and water flows into the fiber. When the relaxing solution is rinsed from the hair with water after eighteen to twenty minutes, the fiber undergoes further swelling. It is this second swelling that frequently causes the fiber cuticle to rupture.

It is believed that application of the deswelling composition reverses the build-up of osmotic pressure on the interior of the fiber. Because the deswelling composition has a high solute (i.e., deswelling composition) concentration in comparison to the interior of the fiber, it causes the osmotic pressure on the exterior of the fiber to be greater than that on the interior of the fiber. As a result, water flows from the interior of the fiber to the exterior, thereby reducing the swelling of the fiber. Therefore, when the lanthionizing solution and the deswelling composition are rinsed from the hair with water the hair does not undergo the further destructive swelling.

The pH-decreasing agent of the deswelling composition is used to strengthen the hair fibers undergoing the relaxing process. The pH-decreasing agent neutralizes the base of the relaxing solution, thereby terminating the lanthionization process while also strengthening the hair because it eliminates osmotic pressure.

Therefore, we have disclosed a novel relaxing process that decreases the swelling of hair fibers and thereby decreases structural damage to the fibers. We have also disclosed a novel deswelling composition utilized in the process.

To establish that the composition and process of the present invention decrease the swelling of hair fibers during the relaxing process, and increase hair fiber strength, four tests were performed.

As a first test, a fiber swelling measurement apparatus was used to measure the respective swelling of hair fibers relaxed according to the conventional process and according to the process of the present invention. A single European Brown hair fiber (obtained from Demeo Brothers, New York, N.Y.) was placed in the demountable flow cell of a stereomicroscope. The stereomicroscope was connected to an Imagen HR diameter measuring device and to a video camera. A 1.325 molar solution of sodium hydroxide was injected into the flow cell, and the fiber swelling measured and recorded over a twenty (20) minute period. After twenty minutes, the sodium hydroxide solution was removed, and deionized water passed through the cell for two minutes, according to the conventional relaxing process. Fiber swelling was measured and recorded.

The results of the fiber swelling analysis for fibers relaxed according to the conventional process are plotted on the graph shown in FIG. 1. The y axis represents the percentage increase of fiber swelling. The x axis represents the time elapsed in minutes from the time the fiber was exposed to the sodium hydroxide solution. As shown in FIG. 1, fiber swelling increased steadily for the entire twenty minutes of exposure to sodium hydroxide. At the lanthionization-swelling peak 10 and time twenty minutes, sodium hydroxide was removed and the fiber rinsed with water for five minutes, according to the conventional relaxing process. As is seen in FIG. 1, the fiber underwent a second-stage swelling during the rinsing stage, with swelling increasing dramatically to a rinsing-swelling peak 12. The rinsing-swelling peak 12 is higher than the lanthionization-swelling peak 10, therefore illustrating the cause of the resulting phenomenon of structural damage to the hair cortex. After the second-stage rinsing swelling reached the rinsing-swelling peak 12, it decreased steadily.

Figure 2:
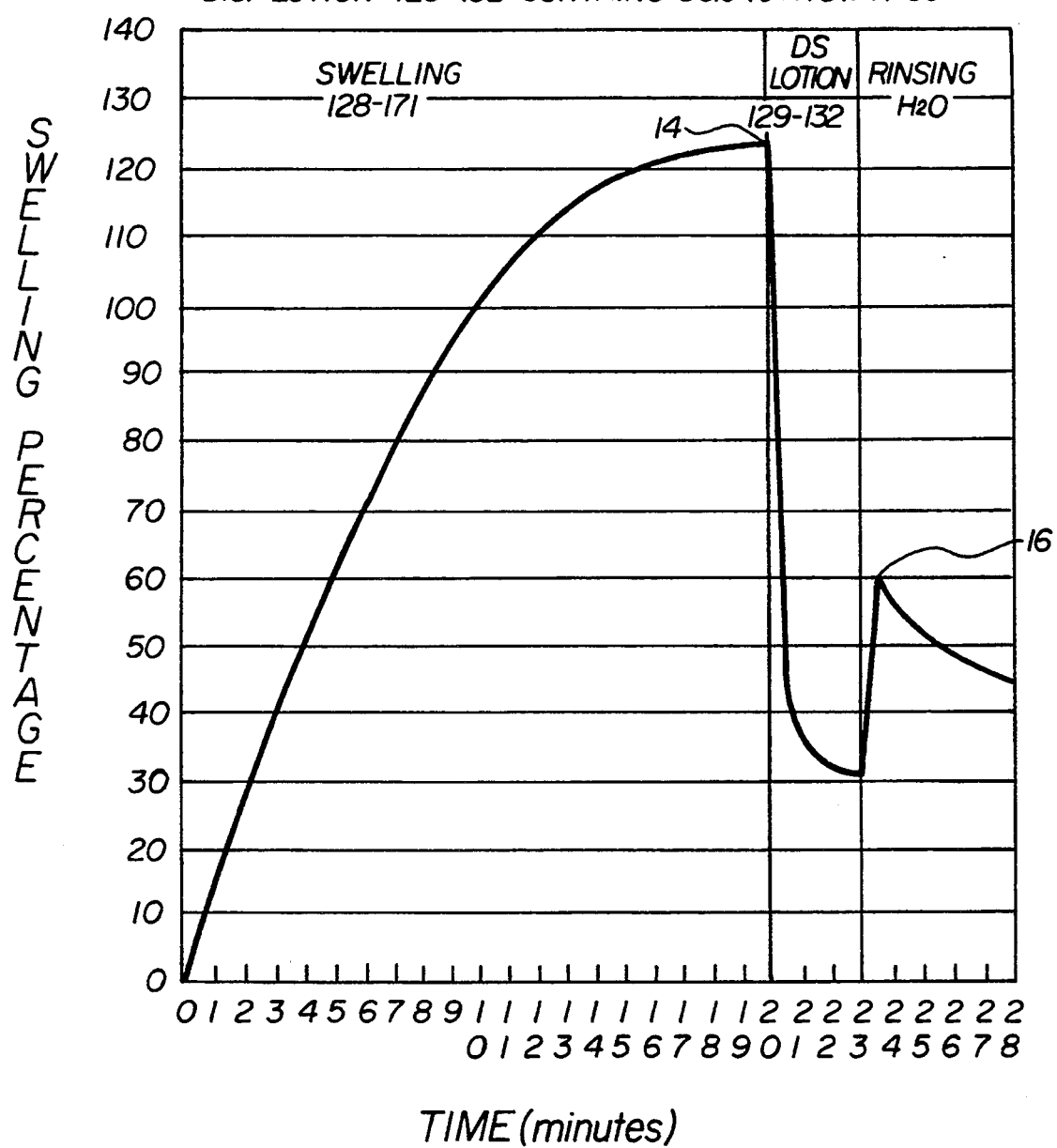
FIG. 2 is a graph illustrating the results of an analysis of the swelling of hair fibers relaxed according to the relaxing process of the present invention.

The test was repeated using the process of the present invention and the composition of the present invention prepared according to Example 5. The results of the fiber swelling analysis are plotted on the graph shown in FIG. 2. As shown in FIG. 2, fiber swelling increased gradually during the period the fiber was exposed to sodium hydroxide alone, to a lanthionization peak 14 at twenty minutes, the point at which the deswelling composition of the present invention was introduced, according to the process of the present invention. The deswelling composition remained on the hair fiber for three minutes, during which fiber swelling decreased dramatically. At the end of three minutes, the fiber was rinsed with water, in accordance with the process of the present invention, and the results plotted. Fiber swelling again increased to a rinsing peak 16. However, because the rinsing peak 16 is lower than the lanthionization peak 14, it is clear that the fibers relaxed according to the process of the present invention are not subject to second-stage swelling greater than first-stage swelling, and therefore are not subject to the resulting structural damage.

A second test was conducted using a real-time scanning electron microscopic study to observe the swelling of hair fibers undergoing the process of the present invention. European Brown hair fibers (obtained from Demeo Brothers, New York, N.Y.) were exposed for 18 minutes at room temperature to a 1,325 molar solution of sodium hydroxide. The hair fibers were then rinsed for five minutes with deionized water, according to the conventional relaxing process. The resulting scanning electron micrographs showed that the fibers had undergone swelling and longitudinal rupture of the fiber cuticles. A second set of European Brown hair fibers (obtained from Demeo Brothers, New York, N.Y.) was also exposed for 18 minutes at room temperature to a 1.325 molar solution of sodium hydroxide. Then, in accordance with the process of the present invention, the composition of the present invention as prepared according to Example 5 was applied to the hair fibers for three to five minutes. The fibers then were rinsed for five minutes with deionized water. The resulting scanning electron micrographs showed that the fibers had undergone minimal swelling and no longitudinal rupture of the cuticles.

A third test was performed to determine the relative tensile strength of hair fibers relaxed according to the conventional process and hair fibers relaxed according to the process of the present invention, including the composition of the present invention as prepared according to Example 5. Two tresses of Afro-American hair fibers (obtained from Demeo Brothers in New York, N.Y.) weighing approximately 2.0 grams each were each treated for eighteen minutes with AFFIRM ® Original No Base Relaxer (available from Avlon Industries, Inc., Chicago, Ill.). The first tress was then rinsed with water for two minutes, according to the conventional process, and shampooed once with a low-pH shampoo. The first tress was then dried until dry with a Solis, Type 311 blow dryer imported from Switzerland by Ross Sales Co., New York, N.Y. and kept at room temperature for twenty-four hours.

After the second tress was treated with AFFIRM ® Original No Base Relaxer for eighteen minutes, two grams of the composition of the present invention (prepared according to Example 5) were applied to the hair for five minutes- The second tress was then rinsed with water for two minutes, and shampooed once with a low-pH shampoo. The second tress was then dried with a blow dryer imported from Switzerland by Ross Sales Co., New York, N.Y. until dry and kept at room temperature for twenty-four hours.

Each tress was then tested for relative tensile strength. using a Dia-Stron Miniature Tensile Tester manufactured by Dia-Stron Limited of the United Kingdom. The test results established that hair fibers relaxed according to the process of the present invention were stronger than those relaxed according to the conventional process.

Finally, to establish that the composition and process of the present invention will be commercially acceptable, tests were performed on twenty-five subjects. In those tests, a subject's hair was parted down the middle so as to form left and right sections. Each section was treated with a commercial sodium hydroxide relaxing solution for thirteen to eighteen minutes. When the hair appeared to be straight, the right side of the head was treated with the composition of the present invention (specifically, the composition prepared as set forth in Example 1) for two to three minutes. The left side of the head was processed according to the conventional relaxing process; specifically, With AFFIRM ® No Base (Original) relaxing solution, available from Avlon Industries, Inc., P.O. Box 388080, Chicago, Ill. 60638.

In accordance with the alternate embodiment of the process of the present invention, the composition of the present invention was then reapplied to the right sides of the subjects' heads for five minutes. The left sides were treated with a commercial conditioner for five minutes, then shampooed once with an acidic shampoo. Both sides were then evaluated subjectively by independent consultants for various properties. The results are set forth in Table 2, wherein the numbers in each line indicate number of subject heads.

The entire test was then repeated using the composition of the present invention as set forth in Example 5. The results the test on ten subject heads are set forth in Table 3.

TABLE 2

| Hair Properties | Hair Relaxed by Conventional Process Has These Properties | Hair Relaxed by Process/ Composition of Present Invention Has These Properties | No Difference | Info. Not Noted |
|---|---|---|---|---|
| Ease of Wet Combing | 0 | 25 | 0 | 0 |
| Wet Feel of Hair (smoother, silkier) | 0 | 25 | 0 | 0 |
| Dry Feel of Hair (smoother, silkier) | 1 | 23 | 1 | 0 |
| Hair Sheen After Drying | 0 | 7 | 14 | 4 |
| Body | 1 | 0 | 22 | 2 |
| Decreased Hair Loss During Combing | 0 | 2 | 23 | 0 |
| Static | 0 | 2 | 23 | 0 |

TABLE 3

| Hair Properties | Hair Relaxed by Conventional Process Has These Properties | Hair Relaxed by Process/ Composition of Present Invention Has These Properties | No Difference | Info. Not Noted |
|---|---|---|---|---|
| Ease of Wet Combing | 0 | 7 | 3 | 0 |
| Wet Feel of Hair (smoother, silkier) | 0 | 6 | 4 | 0 |
| Dry Feel of Hair (smoother, silkier) | 0 | 4 | 6 | 0 |
| Hair Sheen After Drying | 0 | 2 | 8 | 0 |
| Body | 0 | 0 | 8 | 2 |
| Decreased Hair Loss During | 0 | 0 | 8 | 2 |

TABLE 3-continued

| Hair Properties | Hair Relaxed by Conventional Process Has These Properties | Hair Relaxed by Process/ Composition of Present Invention Has These Properties | No Difference | Info. Not Noted |
|---|---|---|---|---|
| Combing Static | 0 | 0 | 8 | 2 |

The results of these tests establish that the composition and process of the present invention decrease the swelling of hair fibers during the relaxing process, resulting in hair that is smoother, silkier, shinier, easier to comb, and more manageable than hair relaxed according to the conventional relaxing process.

In this way, the present invention provides a composition and process that decreases the osmotic swelling of hair fibers during the relaxing process. Accordingly, the composition and process of the present invention prevents structural damage to the hair during the relaxing process, and provides a relaxing process and composition that results in stronger, healthier, and more manageable hair than with the conventional relaxing process.

The present invention has been described with respect to certain embodiments and conditions, which are not meant to and should not be construed to limit the invention. Those skilled in the art will understand that variations from the embodiments and conditions described herein may be made without departing from the spirit and scope of the invention as described in the appended claims.

We claim:

1. A process for relaxing hair fibers comprising the steps of:
   (a) lanthionizing hair fibers with a non-reducing base; and
   (b) applying to the hair fibers a deswelling composition selected from the group consisting of starch, sugar and salt and further comprising a pH- decreasing agent selected from the group consisting of lactic acid and phosphoric acid.

2. The process of claim 1 wherein the deswelling composition comprises a component selected from the group consisting of hydrogenated starch hydrolysates, sodium lactate, glycerol sorbitol, sucrose, glucose, fructose, magnesium sulfate, and sodium acetate.

3. The process of claim 1 wherein the deswelling composition comprises a component selected from the group consisting of hydrogenated starch hydrolysates, sodium lactate, glycerol, sorbitol, sucrose, glucose, fructose, magnesium sulfate, and sodium acetate.

4. The process of claim 1 wherein the deswelling composition has a pH between about 0.5 and about 2.5.

5. The process of claim 1 further comprising the step of:
   (c) rinsing the deswelling composition from the hair with water.

6. The process of claim 5 further comprising the steps of:
   (d) reapplying the deswelling composition to the hair; and
   (e) rinsing the composition from the hair.

7. A composition for decreasing the swelling of hair fibers comprising a component selected from the group consisting of hydrogenated starch hydrolysates, sodium lactate, glycerol, sorbitol, sucrose, glucose, fructose, magnesium sulfate, and sodium acetate and further comprising a pH- decreasing agent selected from the group consisting of lactic acid and phosphoric acid.

8. A composition for decreasing the swelling of hair fibers during the relaxing process comprising
   (a) between about 10 and about 95 parts by weight of a hydrogenated starch hydrolysate;
   (b) between 0.00 and about 12.00 parts by weight of a noncaustic acid;
   (c) between about 0.25 and about 5.0 parts by weight of a cationic polymer; and
   (d) between about 0.1 and about 5.0 parts by weight ethoxylated fatty acid.

9. The composition of claim 8 wherein the non-caustic acid is selected from the group consisting of phosphoric acid and lactic acid.

* * * * *